（12）United States Patent
Mestres et al.

(10) Patent No.: US 7,696,190 B2
(45) Date of Patent: *Apr. 13, 2010

(54) 16ALPHA-METHYL OR ETHYL SUBSTITUTED ESTROGENS

(75) Inventors: Jordi Mestres, Scotland (GB); Hubert Jan Jozef Loozen, Uden (NL); Gerrit Herman Veeneman, Schaijk (NL)

(73) Assignee: N.V. Organon, Oss (NL)

( * ) Notice: Subject to any disclaimer, the term of this patent is extended or adjusted under 35 U.S.C. 154(b) by 217 days.

This patent is subject to a terminal disclaimer.

(21) Appl. No.: 10/343,293

(22) PCT Filed: Jul. 23, 2001

(86) PCT No.: PCT/EP01/08535

§ 371 (c)(1),
(2), (4) Date: Jul. 17, 2003

(87) PCT Pub. No.: WO02/10188

PCT Pub. Date: Feb. 7, 2002

(65) Prior Publication Data

US 2004/0043976 A1     Mar. 4, 2004

(30) Foreign Application Priority Data

Jul. 28, 2000   (EP)   .................. 00202697

(51) Int. Cl.
*A61K 31/56* (2006.01)
*C07J 1/00* (2006.01)
*C07J 7/00* (2006.01)

(52) U.S. Cl. .................. 514/182; 552/642; 552/644; 552/645; 552/649; 552/558

(58) Field of Classification Search .................. 514/182, 514/178, 169; 552/642, 644, 645, 649
See application file for complete search history.

(56) References Cited

U.S. PATENT DOCUMENTS

| | | | |
|---|---|---|---|
| 3,007,946 A | 11/1961 | Tyner | |
| 3,049,555 A | 8/1962 | Tyner | |
| 3,092,645 A | 6/1963 | Nicholson | |
| 3,257,429 A | 6/1966 | Ringold et al. | |
| 3,299,108 A | 1/1967 | Baran | |
| 3,377,366 A | 4/1968 | Baran | |
| 3,464,979 A | 9/1969 | Barton | |
| 3,465,010 A | 9/1969 | Baran | |
| 3,652,606 A | 3/1972 | Baran | |
| 3,704,253 A | 11/1972 | Stein et al. | |
| 4,272,530 A | 6/1981 | Teutsch et al. | |
| 5,116,830 A * | 5/1992 | Tanabe et al. | 514/182 |
| 5,273,971 A * | 12/1993 | Scholz et al. | 514/176 |
| 6,541,465 B2 * | 4/2003 | Loozen et al. | 514/178 |
| 6,677,329 B1 * | 1/2004 | Loozen et al. | 514/182 |
| 6,780,854 B2 * | 8/2004 | Loozen et al. | 514/178 |
| 6,989,378 B2 * | 1/2006 | Leysen et al. | 514/178 |
| 2005/0153949 A1 * | 7/2005 | Leysen et al. | 514/178 |

FOREIGN PATENT DOCUMENTS

| | | |
|---|---|---|
| DE | 10 84 261 B | 6/1960 |
| DE | 2757157 | 6/1979 |
| EP | 0 145 493 | 3/1989 |
| EP | 0 613 687 | 9/1994 |
| GB | 890 989 A | 3/1962 |
| GB | 1 341 601 A | 12/1973 |
| WO | WO 94/18224 | 8/1994 |
| WO | WO 99/45886 | 9/1999 |
| WO | WO 00/31112 | 6/2000 |
| WO | 01/18027 * | 3/2001 |

OTHER PUBLICATIONS

H. Takikawa et al: "The Competitive action of 16.beta.-Ethylestradiol on the Binding of Estrogen Receptor in Human Breast Cancer"; vol. 7, 1977, pp. 291-299.

Fevig T L et al: "Estrogen Receptor Binding Tolerance of 16-Alpha-Substituted Estradiol Derivatives", Steroids, vol. 51, No. 5-6, 1988, pp. 471-498.

Baggett B et al: "Effects of 2 Metabolites of Norethynodrel on Reproductive Performance of Female Rats" Fertility and Sterility, vol. 21, No. 1, 1970.

Tedesco R et al: "7alpha, 11beta-disubstituted estrogens: probes for the shape of the ligand binding pocket in the estrogen receptor" Bioorganic & Medicinal Chemistry Letters, GB, Oxford, vol. 7, No. 22, Nov. 18, 1997, pp. 2919-2924.

(Continued)

*Primary Examiner*—Sabiha N. Qazi
(74) *Attorney, Agent, or Firm*—Susan Hess

(57) ABSTRACT

The invention makes a 16α-substituted steroidal compound available having formula 1, wherein the dotted ring is a fully saturated, a fully aromatic or a saturated ring with a Δ5-10 double bond; $R^1$ is $(C_1-C_3)$alkyl or $(C_2-C_3)$alkenyl, and each of these groups can be substituted with one or more halogens; $R^2$ is $(C_1-C_4)$alkyl, $(C_2-C_4)$alkenyl or methylene, and each of these groups can be substituted with one or more halogens; $R^3$ is methyl or ethyl; or a prodrug thereof, which compound can be used for an estrogen receptor α selective treatment (1)

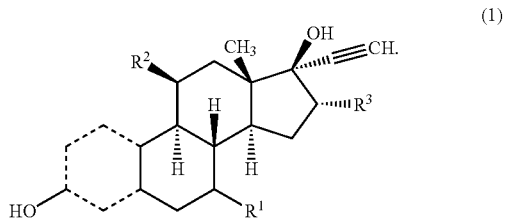

4 Claims, No Drawings

OTHER PUBLICATIONS

English language abstracts of DE2757157.

Avery et al., "Synthesis and Testing of 17αβ-hydroxy-7α-methyl-D-homoestra-4,16-dien-3-one: A Highly Potent Orally Action Androgen," Steroids 55 (1990) 59-64.

González et. al., "Synthesis and Pharmacological Evaluation of 8α-Estradiol Derivatives," *Steroids* 40 (1982) 171-187.

Solo et al., "7α-Alkyltestosterone Derivatives: Synthesis and Activity as Androgens and as Aromatase Inhibitors," Steroids 40 (1982) 603-614.

* cited by examiner

16ALPHA-METHYL OR ETHYL SUBSTITUTED ESTROGENS

FIELD OF THE INVENTION

This invention relates to a 16α-substituted steroidal compound, to a method of activating estrogenic receptors with such a compound and to the use of such a compound for the manufacture of a medicine for estrogen-receptor related treatments.

BACKGROUND OF THE INVENTION

Steroidal compounds with estrogenic activity have found long-standing utility in the treatment of a variety of medical indications and in regimes for contraceptive purposes. Despite the long history of the field there still is a need for more effective, safer and more economical compounds than the existing ones. This need is the more pressing in view of advancement in health care in other areas, which has led to an increasingly longer life span. This is in particular a problem for women for whom the decline in estrogenic hormones at menopause is drastic and has negative consequences for bone strength and cardiovascular functions. For estrogenic treatment, there are highly active estrogenic 16α-substituted estragenic steroids available as for example described in Fevig et al (in Steroids 51: PP 471-497, 1988), DE 2757157, U.S. Pat. No. 3,704,253 and Takikawa et al (in Res. Steroids Vol 7, pp 291-299, 1977). Also 7α,11β-disubstituted estrogens are known from Tedesco et al (in Bioorganic & Medicinal Chemistry Letters, Vol 7, No 22, pp 2919-2924, 1997), but further improvements are still possible in this field. The discovery of subtypes of estrogen receptors, there being an α-subtype (ER α) and a β-subtype (ER β) of such receptors, offers the possibility for more selective activation of one particular subtype of those two receptors, immanently resulting in more effective treatments or treatments with less side effects. Specifically 16β-methyl-estrogens are described in González et al (Steroids Vol. 40; 171-187; 1982), but compounds with the 16β-configuration do not generally have the favourable selective effect of a compound of this invention.

DETAILED DESCRIPTION OF THE INVENTION

The present invention is based on the discovery of compounds, which are unexpectedly selective for the estrogen receptor of the α-subtype. This invention makes a 16α-substituted steroidal compound available having formula 1,

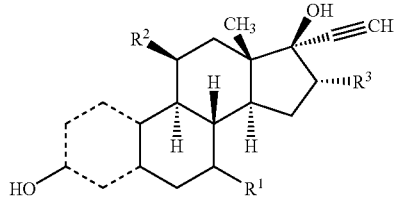

formula 1 wherein:
the dotted ring (so-called A-ring) is a fully saturated, a fully aromatic or a saturated ring with a Δ5-10 double bond;
$R^1$ is $(C_1-C_3)$alkyl or $(C_2-C_3)$alkenyl, and each of these groups can be substituted with one or more halogens;
$R^2$ is $(C_1-C_4)$alkyl, $(C_2-C_4)$alkenyl or methylene, and each of these groups can be substituted with one or more halogens;
$R^3$ is methyl or ethyl.

The bonds at the 3 and 7 position, for which the stereochemistry in formula 1 is not specified, can independently be either in α or in β position with respect to the steroid skeleton. Obviously, when $R^2$ is methylene the bond at the 11 position is not meant to be in β configuration.

A preferred halogen in $R^2$ is chlorine or fluorine.
A preferred selection for $R^2$ is $(C_1-C_2)$alkyl or vinyl.
Of course, the invention also makes prodrugs for the above defined compounds available.

A prodrug is defined as being a compound, which converts in the body of a recipient to a compound as defined by formula 1. Notably, the hydroxy groups as depicted in the formulas above can for example be substituted by alkyl*oxy, alkenyl*oxy, acyl*oxy, aroyloxy, alk*oxycarbonyloxy, sulfonyl groups or phosphate groups, whereby the carbon chain length of the groups denoted with an asterisk (*) is not considered to be sharply delimited, while aroyl generally will comprise a phenyl, pyridinyl or pyrimidyl. Preferred prodrugs are carboxylic acid esters or alkyl ethers on one or both hydroxyl groups, and more preferred prodrugs are $(C_2-C_6)$ carboxylic acid esters, such as esters of (iso)butanoic acid, or $(C_1-C_4)$ alkyl ethers. The length of the alkyl, alkenyl and acyl groups is selected depending on the desired properties of the prodrugs, whereby the longer chained prodrugs with for example lauryl or caproyl chains are more suitable for sustained release and depot preparations. It is known that such substituents spontaneously hydrolyse or are enzymatically hydrolysed to the free hydroxyl substituents on the skeleton of the compound. Such prodrugs will have biological activity comparable to the compounds to which they are converted in the body of the recipients. The active compound to which a prodrug is converted is called the parent compound. The onset of action and duration of action as well as the distribution in the body of a prodrug may differ from such properties of the parent compound. For other types of prodrugs it should be realised that the hydroxyl groups in formula 1 can be placed in position by the metabolic system of the recipient. The hydroxyl groups are essential for affinity for the estrogen receptors. Thus, compounds as defined by formula 1, but lacking one or both hydroxyl groups are also made available as compounds according to this invention, and to which compounds is referred as prodrugs.

Other terms used in this description have the following meaning:
alkyl is a branched or unbranched alkyl group, for example methyl, ethyl, propyl, butyl or sec-butyl;
alkenyl is a branched or unbranched alkenyl group, such as ethenyl, 2-butenyl, etc.;
halogen refers to fluorine, chlorine, bromine and iodine;
aroyl is arylcarbonyl such as a benzoyl group;
aryl is a mono- or polycyclic, homo- or heterocyclic aromatic ring system;
acyl is an alkylcarbonyl group.

The prefixes $(C_1-C_4)$, $(C_2-C_4)$ etceteras have the usual meaning to restrict the meaning of the indicated group to those with respectively 1 to 4, 2 to 4 etc. carbon atoms.

The selective estrogen-receptor affinity profile of the compounds according to the present invention makes them suitable for use in therapy. The compounds are suitable as improved estrogens, in the sense that they can be used for estrogen-receptor related medical treatments, such as those for contraception or for treatment or prevention of benign prostate hypertrophy, cardiovascular disorders, menopausal complaints, osteoporosis, estrogen dependent tumour control or central nervous system disorders such as depression or Alzheimer's disease.

Therefore, the invention relates to the use of a compound according to the invention for the manufacture of a medicament for a selective estrogen-receptor related treatment. The selective estrogen-receptor related treatment is obtained by activation of the α-subtype of the estrogen receptors. Such a medicament can be used for treatment of estrogen-receptor related disorders such as peri- and/or post-menopausal complaints and also making the medicament generally suitable in the area of hormone replacement therapy (HRT). The treatment comprises administration of the compound according to the present invention to an organism with both subtypes of receptors. Thus the invention also pertains to a method of treatment for selective activation of estrogen receptors of the α-subtype comprising the administration of a compound according to the invention to a recipient in a suitable amount. Such a method of treatment is suitable for the medical indications of peri- and/or post-menopausal (climacteric) complaints and osteoporosis, i.e. a method of treatment in the field of hormone replacement therapy.

An organism that can be a recipient of a selective estrogenic treatment can be an animal or human being, and in usually will be a female animal or a woman in need of estrogenic treatment.

Administration of a compound according to the invention will be greatly aided by manufacture of pharmaceutical compositions. The present invention, therefore, also relates to a pharmaceutical composition comprising a compound according to the invention mixed with a pharmaceutically acceptable auxiliary.

In a particular aspect the invention relates to the use of a compound according to the invention in the manufacture of a medicament having contraceptive activity. Thus the invention also pertains to the medical indication of contraception, i.e. a method of contraception comprising the administration of a compound according to the invention in a suitable amount to a recipient, being a woman or a female animal, of a progestogen and an estrogen as is customary in the field, wherein the estrogen is a compound as described herein before (in a suitable pharmaceutical dosage form).

The compounds of the invention can be produced by various methods known in the art of organic chemistry of steroids in general. Introduction of 16α methyl or ethyl groups to steroids is easily done by methods known in organic synthetic literature. Generally, an anion at position C-16 can be formed by treatment of C-17-ketones with appropriate bases such as alkali metal salts of organic secondary amines (diisopropylamine or hexamethyldisilazane). Treatment of these anions with alkylating agents like alkylhalides leads to the desired 16α-alkylated steroids. Alternative methods of alkylation are available, for example, starting with conversion of a C17-carbonyl steroid into the corresponding hydrazone followed by the formation of the C16-anion, alkylation, followed by liberation of the carbonyl by cleavage of the hydrazone. Alternatively, the anion at position 16 is formed by conjugated reduction of a Δ15-en-17-one steroid with alkalimetals. More specifically the routes of synthesis as illustrated in the schemes and examples can be used.

Ester prodrugs can be made by esterification of compounds with free hydroxyl groups by reaction with appropriate acyl chlorides in pyridine.

Methods of preparation of a pharmaceutical composition are described in the standard reference Gennaro et al., *Remmington's Pharmaceutical Sciences*, (18th ed., Mack publishing Company, 1990, see especially Part 8: Pharmaceutical Preparations and Their Manufacture) and suitable auxiliaries are made available in e.g. the Handbook of Pharmaceutical Excipients ($2^{nd}$ Edition, Editors A. Wade and P. J. Weller; American Pharmaceutical Association; Washington; The Pharmaceutical Press; London, 1994). The mixture of the compound according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

A method of treatment according to this invention comprises the administration to an animal or human person of a compound as described herein before (in a suitable pharmaceutical dosage form). A suitable dosage amount of the present compounds will be of the normal order for estrogenic compounds, e.g. of the order of 0.01 to 100 mg per administration.

The invention is further illustrated hereinafter with reference to some unlimitative examples and the corresponding formula schemes referred to.

EXAMPLES

The compound numbers refer to corresponding structural formulas in the schemes 1 and 2.

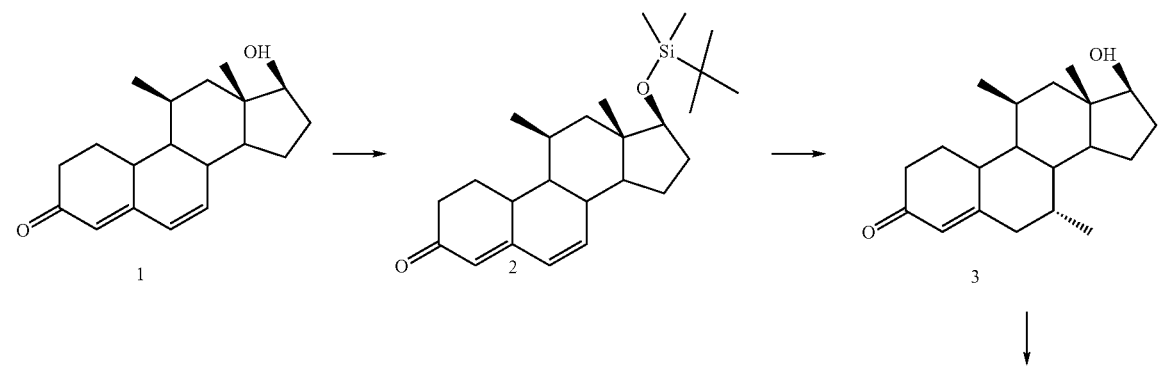

Scheme 1

-continued

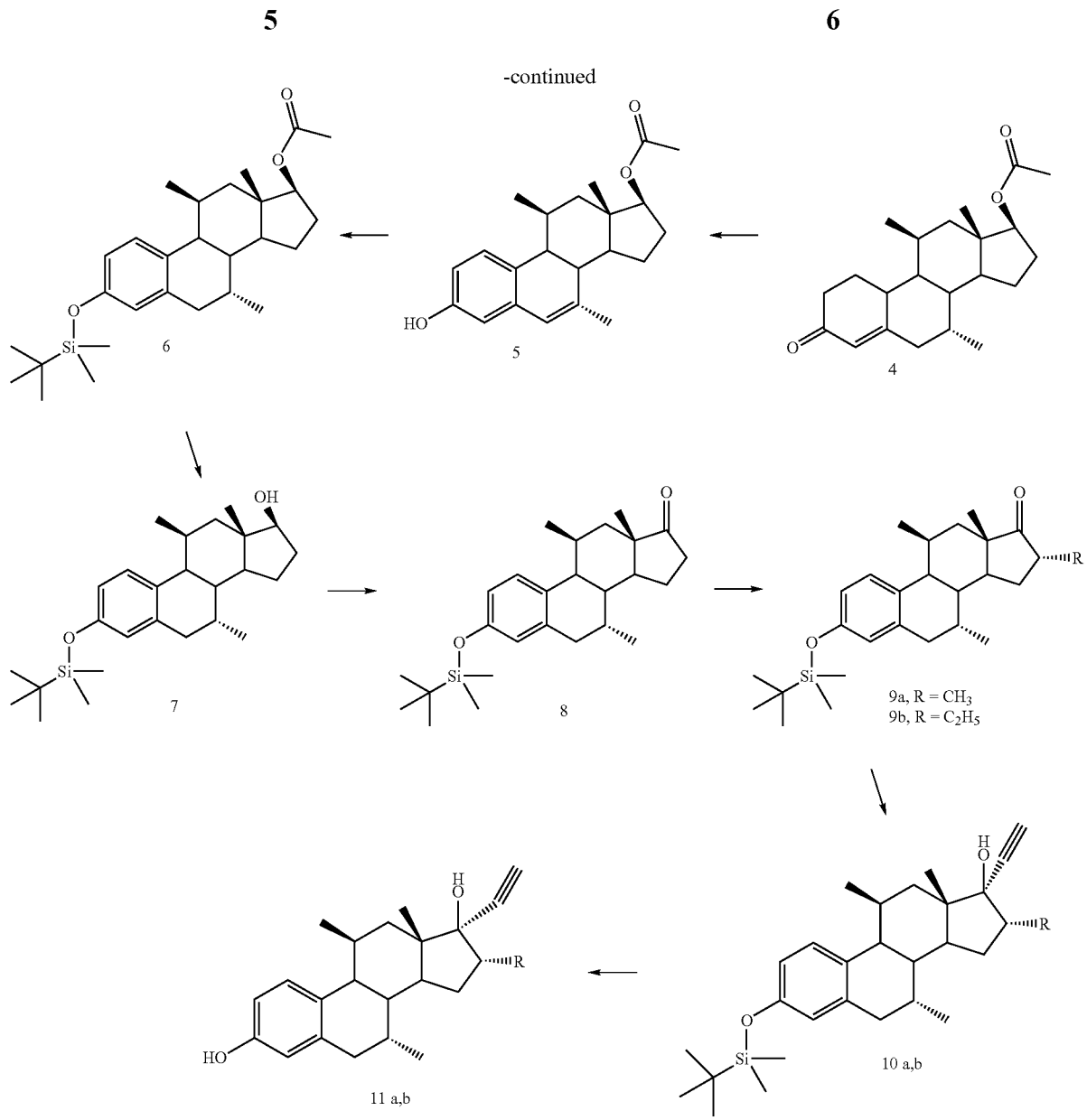

All NMR spectra were recorded as solutions in CDCl$_3$ in a 400 MHz spectrometer.

Compound 2

A solution of 13 ml of tert.butyldimethylsilyl chloride in 20 ml of diethylether was added dropwise to a mixture of 15 g of 11β-methyldienolone 1 and 14 g of imidazole in 150 ml of DMF at 0° C. After stirring for 2 h the reaction was complete. Water was added and the product extracted with ethyl acetate. The material thus obtained was purified by passing through a short silica column, to provide 17 g of 2; R$_f$ 0.56 (heptane/ethyl acetate 7/3), NMR δ1.1 (d, 3, 11β CH$_3$), 0.91 (s, 3, 18-CH$_3$), 3.55 (m, 1, 17αH), 5.80 (m, 1, H4), 6.21 (s, 2, H6,H7).

Compound 3

To a solution of 20.5 g of steroid 2 and 2 g of cupricacetate in 500 ml of dry THF was added dropwise at −30° C. 40 ml of a 22% solution of methylmagnesium chloride in THF over a period of ¾ h. The reaction mixture was subsequently stirred for an additional ½ h and then poured into a solution of 30 ml of conc sulphuric acid in 100 ml of water. The mixture was stirred for another 16 h, then 19 g of NaOAc were added and the product was extracted with ethyl acetate. The 7α isomer was purified by chromatography over silica, to give 8.5 g of pure 3, R$_f$ 0.45 (heptane/ethyl acetate 1/1), 7β-isomer at R$_f$ 0.42; NMR δ 1.07 (d, 3, 11β-CH$_3$), 0.88 (s, 3, 18-CH$_3$), 0.78 (d, 3, 7α-CH$_3$).

Compound 4

A mixture of 5.5 g of 3, 15 ml of pyridine, 4.7 ml of acetic anhydride and 40 mg of DMAP was stirred at room temperature for 1 h. Then water was added and the product extracted with ethyl acetate. The organic layer was washed with 2N HCl to remove pyridine and then with water. The residue obtained after drying and concentration was used as is in the next step. R$_f$ 0.59(heptane/ethyl acetate 1/1), NMR: δ 1.06 (d, 3, 11β-CH$_3$), 0.92 (s, 3, 18-CH$_3$), 0.78 (d, 3, 7α-CH$_3$), 2.04 (s, 3, acetate), 4.56 (dd, 1, H17α) 5.84 (broad s, 1, H4).

Compound 5

To a solution of 6.2 g of 4 in 180 ml of dry acetonitrile was added 1.6 g of LiBr followed by 8 g of $CuBr_2$. After stirring for 2 h the aromatization reaction was completed. The mixture was diluted with 400 ml of water and extracted with ethyl acetate. The organic layer was washed with water and 5% aquous $NaHCO_3$ solution and dried and concentrated. Chromatographic purification provided 4.2 g of 5, $R_f$ 0.67 (heptane/ethyl acetate 1/1), NMR δ 0.84 (d, 3, 11β-$CH_3$), 0.93 (s, 3, 18-$CH_3$), 0.81 (d, 3, 7α-$CH_3$), 2.05 (s, 3, acetate), 4.64 (dd, 1, H17α) 6.52 (d, 1, H4), 6.62 (AB, 1, H2), 7.03 (AB, 1, H1).

Compound 6

To a solution of 4.2 g of 5 in 20 ml of DMF was added at 0° C. 1.7 g of imidazole, followed by 2.2 g of TBDMS-Cl. The mixture was stirred for several hours at room temperature and after completion of the silylation poured into 150 ml of water. The product was extracted with with ethyl acetate. The product thus obtained was passed through a short silica column and provided 4.5 g of 6, $R_f$ 0.77 (heptane/ethyl acetate 7/3), NMR δ 0.84 (d, 3, 11β-$CH_3$), 0.94 (s, 3, 18-$CH_3$), 0.80 (d, 3, 7α-$CH_3$), 0.98 (s, 9, tert.$C_4H_9$Si), 0.18 (s, 6, Si($CH_3$)$_2$), 2.06 (s, 3, acetate), 4.64 (dd, 1, H17α) 6.49 (d, 1, H4), 6.59 (AB, 1, H2), 7.00 (AB, 1, H1).

Compound 7

A solution of 5.4 g of 6 in 10 ml of THF was added dropwise to a stirred suspension of 400 mg of $LiAlH_4$ in 20 ml of THF. After stirring for 15 min the reduction was complete and the mixture was treated first with 1.1 ml of sat $Na_2SO_4$, and then with 8 g of $Na_2SO_4$, followed by filtration over Celite and concentration to provide 4.5 g of 7, $R_f$ 0.50 (heptane/ethyl acetate 7/3), ), NMR δ 0.85 (d, 3, 11β-$CH_3$), 0.90 (s, 3, 18-$CH_3$), 0.80 (d, 3, 7α-$CH_3$), 0.97 (s, 9, tert.$C_4H_9$Si), 0.18 (s, 6, Si($CH_3$)$_2$), 3.70 (dd, 1, H17α).

Compound 8

To a solution of 4.5 g of 7 and 3.4 g of NMO in 50 ml of acetone was added 100 mg of TPAP. After stirring for 1 h the oxidation was complete. To the reaction mixture was added 5 g of silica gel, followed by 90 ml of heptane. The mixture was stirred for 15 min and then filtered through Celite. The filtrate was concentrated and passed through a short silica path and provided 3.7 g of 8, $R_f$ 0.66 (heptane/ethyl acetate 7/3), NMR δ 0.86 (2×d, 6, 7α+11β-$CH_3$), 1.01 (s, 3, 18-$CH_3$), 0.98 (s, 9, tert.$C_4H_9$Si), 0.19 (s, 6, Si($CH_3$)$_2$) 6.53 (d, 1, H4), 6.62 (AB, 1, H2), 7.01 (AB, 1, H1).

Compound 9a

A solution of 1 g of steroid 8 and 0.64 ml of DMPU in 20 ml of dry THF was added dropwise at −45° C. to a solution of 2.66 ml of 1M LiHMDS in 10 ml of THF. After stirring for an additional ½ h at −45° C., 0.20 ml of methyliodide was added and stirring prolonged at −20° C. until completion of the alkylation (½ h). Then 200 ml of 10% aq. $NH_4Cl$ was added and the the product extracted with ethyl acetate. Upon further purification of the material by chromatography 0.88 g of 16α alkylated material 9a was obtained. $R_f$ 0.70 (heptane/ethyl acetate 7/3), NMR δ 0.86 (2×d, 6, 7α+11β-$CH_3$), 1.05 (s, 3, 18-$CH_3$), 0.97 (s, 9 tert.$C_4H_9$Si), 0.19 (s, 6, Si($CH_3$)$_2$) 1.14 (d, 3, 16α$CH_3$) 6.53 (d, 1, H4), 6.62 (AB, 1, H2), 7.01 (AB, 1, H1).

Compound 9b

Preparation carried out in the same way as described for 9a, but using 0.25 ml of ethyliodide as the alkylating agent. Reaction was stirred for several hrs at room temperature to go to completion. Chromatography provided 0.84 g of 9b, $R_f$ 0.75 (heptane/ethyl acetate 7/3), NMR δ0.86 (2×d, 6, 7α+11β-$CH_3$), 1.05 (s, 3, 19-$CH_3$), 0.97 (s, 9 tert.$C_4H_9$Si), 0.96 (t, 3, 16α $CH_3CH_2$—), 0.19 (s, 6, Si($CH_3$)$_2$) 6.53 (d, 1, H4), 6.62 (AB, 1, H2), 7.01 (AB, 1, H1).

Compound 10a

A solution of Li-acetylide was prepared by dropwise addition of 10.3 ml of 1.6 M of BuLi/hexane to a solution of 0.67 ml of 1,2-dibromoethene in 20 ml of dry THF at −60° C. After stirring for an additional ½ h a solution of 0.88 g of 9a in 5 ml of THF was introduced and the reaction mixture was gradually warmed to room temperature. After stirring for 1 h the reaction was complete and the mixture poured into 10% aq $NH_4Cl$ solution. The product was extracted with ethyl acetate and purified by chromatography, to provide 790 mg of 10a, $R_f$ 0.23 (heptane/ethyl acetate 9/1), NMR δ0.80 (d, 3, 7α$CH_3$), 0.87 (d, 3, 11β$CH_3$), 1.05 (s, 3, 19-$CH_3$), 0.97 (s, 9, tert.$C_4H_9$Si), 0.19 (s, 6, Si($CH_3$)$_2$) 1.20 (d, 3, 16α$CH_3$) 2.68 (s, 1, acetylene).

Compound 10b

Reaction carried out in the same way as described for 10a, using 0.84 g of 9b, to provide 710 mg of 10b, $R_f$ 0.24 (heptane/ethyl acetate 9/1), NMR δ0.79 (d, 3, 7α$CH_3$), 0.88 (d, 3, 11β$CH_3$), 0.98 (t, 3, 16α $CH_3CH_2$—), 0.96 (s, 9 tert.$C_4H_9$Si), 0.19 (s, 6, Si($CH_3$)$_2$) ), 2.65 (s, 1, acetylene).

Compound 11a

To a solution of 790 mg of 10a in 1 ml of THF was added 2.5 ml of 1M TBAF in THF. After stirring for 10 min the deprotection was complete. Water was added and the product extracted into ethylacetate and finally purified by passing through a silica pad. The material thus obtained was triturated with heptane-diisopropyl ether (1/1) to provide 480 mg of essentially pure 11a, $R_f$ 0.31 (heptane/ethyl acetate 7/3), Mp 204-205° C., NMR δ0.81 (d, 3, 7α$CH_3$), 0.88 (d, 3, 11β$CH_3$), 1.05 (s, 3, 18-$CH_3$), 1.20 (d, 3, 16α$CH_3$) 2.69 (s, 1, acetylene).

Compound 11b

Compound 11b was prepared similarly as described for 11a, using 710 mg of 10b. Precipitation of the final product from ethanol/water provided 430 mg of essentially pure 11b, $R_f$ 0.30 (heptane/ethyl acetate 7/3), ), NMR δ0.80 (d, 3, 7α$CH_3$), 0.88 (d, 3, 11β$CH_3$), 1.00 (t, 3, 16α $CH_3CH_2$—), 1.06 (s, 3, 18-$CH_3$) 2.65 (s, 1, acetylene).

Example 2

The synthesis of the compound (3α,11β,16α,17β)-16-methyl-11-(2-propenyl)-19-norpregn-5(10)-en-20-yne-3,17-diol (compound 27) is described with reference to scheme 2 (next page).

Scheme 2
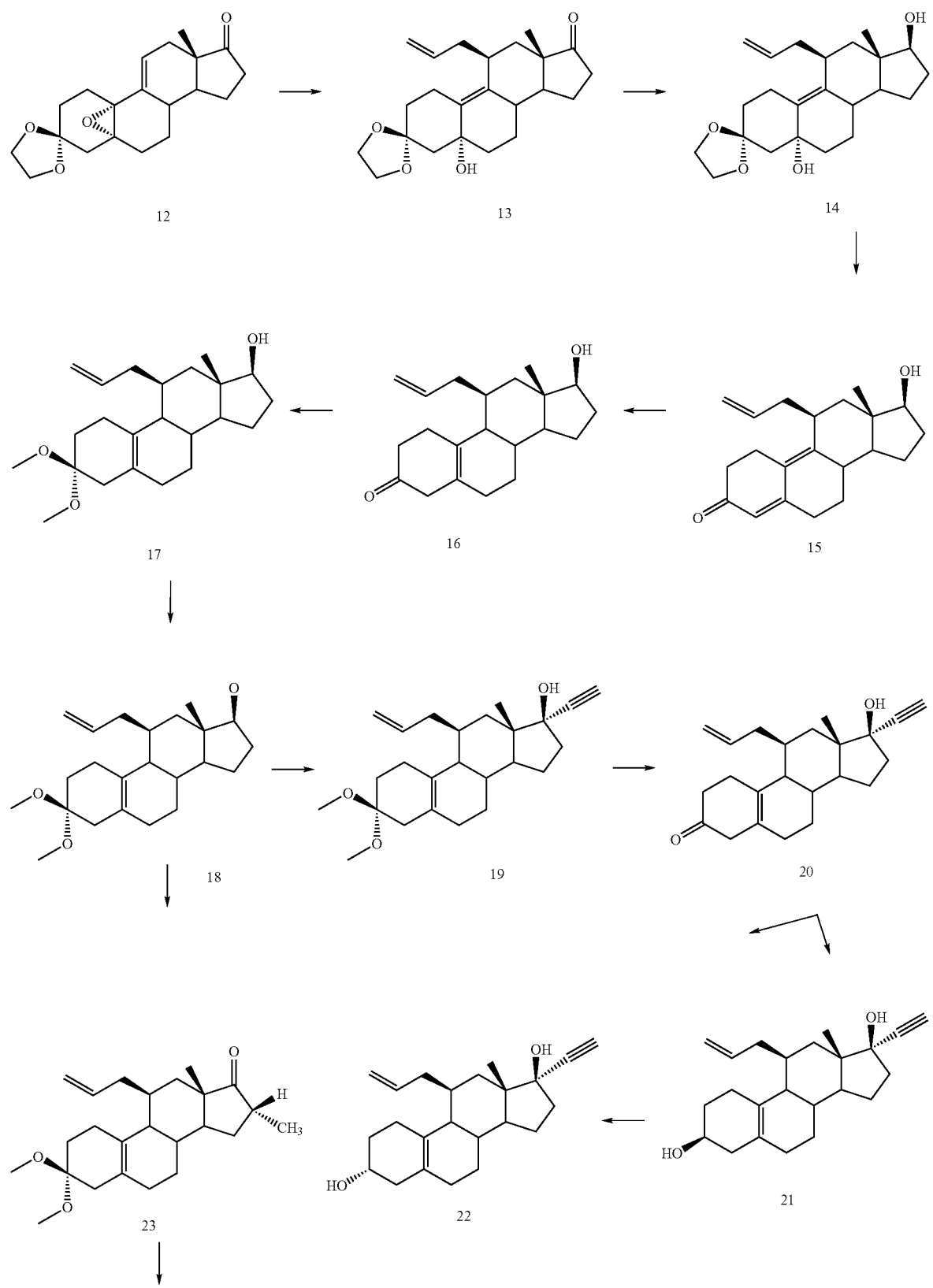

-continued

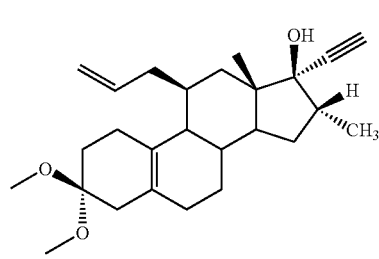

24

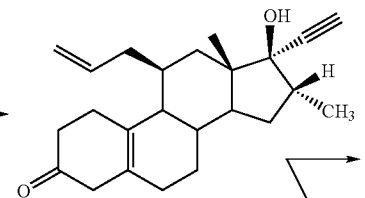

25

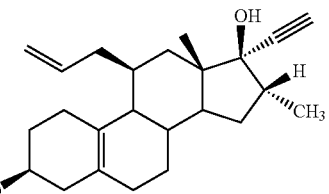

26

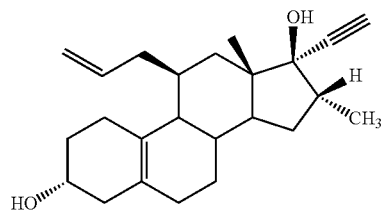

27

Compound 13

To a solution of 17.3 g of CuI and 3.84 g of LiCl in 250 ml of dry THF was added at −70° C. 90.6 ml of a 1M solution of allylmagnesium bromide in diethyl ether. After stirring for an additional 20 min. 11.4 ml of trimethylchlorosilane was added followed by a solution of 7.5 g of steroid 12 in 100 ml of THF. The reaction mixture was kept all the time below −60° C. After stirring for 1 h the reaction was quenched by pouring into sat. aqueous $NH_4Cl$ solution. The product was extracted with ethyl acetate and subsequently purified by column chromatography to provide 6.25 g of 13 as a colorles oil. NMR 5.20 (m, CH allyl); 5.0 ($CH_2$, allyl); 3.04 (m, H11).

Compound 14

To a solution of 9.6 g of 13 in a mixture of 100 ml of methanol and 30 ml of methylene chloride, containing 800 mg of NaOH, was added 0.4 g of sodium borohydride at 0-5° C. After stirring for 1.5 h the reaction was complete and the mixture was treated with 20 ml of acetone for 0.5 h.

The reaction was then poured into water and extracted with ethyl acetate, to provide 9.5 g of 14. NMR 3.59 (t, CHOH); 2.98 (m, H11), 0.92 (s, $CH_3$).

Compound 15

To a solution of 9.5 g of 14 in 100 ml of acetone was added 8 ml of 6 N HCl. After stirring for 2 h. The mixture was neutralized with $NaHCO_3$ and concentrated to a small volume, diluted with water and extracted with ethyl acetate. This provided 8.2 g of 15 as a colorless amorphous material. NMR 5.68 (m, H4); 3.10 (m, H11); 3.65 (m, CHOH).

Compound 16

A solution of 8.2 g of 15 in 100 ml of dry THF was added to 500 ml of liq. $NH_3$ at −70° C. This mixture was treated with an amount of lithium metal (about 500 mg) until the blue color of the reaction mixture persisted for at least 15 min. The reaction was quenched by addition of a portion of $NH_4Cl$.

The residue which remained after evaporation of the $NH_3$ was diluted with water and extracted with ethyl acetate. Chromatographic purification provided 4.0 g of 16 as a colorless oil; $R_f$ 0.55 (hept./ethylacetate 1/1 v/v).

NMR 2.80 (ab, CH2 at C4); 0.93 (s, CH3).

Compound 17

To a solution of 4.0 g of 16 in 80 ml of methanol was added 6 ml of trimethylorthoformate, followed by 0.8 g of toluene-sulfonic acid. After stirring for 2 hr the ketalization was completed. The mixture was treated with 6 ml of pyridine and concentrated to a small volume. The remainders were diluted with water and extracted with ethyl acetate. The residue 4.7 g, consisted of almost pure 17; tlc, $R_f$ 0.78 (hept./ethylacetate 1/1, v/v).

NMR 3.22, 3.25 (2×s, $OCH_3$).

Compound 18

To a solution of 33 g of 17 in 50 ml of acetone was added 6 gr of mol sieves (4A) followed by 3.2 g of N-methylmorpholine-N-oxide and 150 mg of tetrapropylammonium perruthenate. The mixture was stirred for 1 h. To the reaction mixture was added 5 g of silica gel followed by 50 ml of heptane and was stirred for an additional 5 min. The mixture was filtered over hy-flow, and after concentration in part it was taken up in ethylacetate, washed with water, and concentrated. The residue was passed over a short silica column and provided 2.9 g of 18. $R_f$ 0.52 (heptane/ethylacetate 7/3).

NMR 1.02 (s, $CH_3$).

Compound 19

For the ethinylation lithiumacetylide was prepared from dibromoethene and butyllithium.

To a solution of 0.74 ml of 1,2-dibromoethene in 20 ml of THF was added at −70° C. 11 ml of a 1.6 M solution of BuLi in hexane. After stirring for 15 min. a solution of 800 mg of 18 in 2 ml of THF was added. The mixture was allowed to warm to room temperature in 15 min, and after an additional 15 min. at room temperature the reaction was quenched with water and the product extracted with ethyl acetate. Concentration followed by passing through a short silica gel column gave 810 mg of 19 as a white amorphous material. $R_f$ 0.48 (heptane-ethyl acetate 7/3), $R_f$ starting material 0.52. NMR 2.61 (s, acetylene).

Compound 20

To a suspension of 3.2 g of 19 in 60 ml of ethanol was added 0.16 g of oxalic acid in 16 ml of water. The mixture was stirred for 2.5 hr and became gradually homogeneous. The reaction mixture was treated with NaHCO$_3$ and concentrated to a small volume. Then water was added and the product was extracted with ethyl acetate. The crude product thus isolated was passed through a short silica gel column and crystallized from diisopropylether, to provide 2.3 g of 20, Mp 136° C. R$_f$ 0.66 (heptane-ethyl acetate 1/1). NMR 2.78 (ab, 2, H4); 2.61 (s, acetylene).

Compounds 21, 22

To a solution of 1 g of 20 in 12 ml of THF was added 1.6 g of lithium tri-t-butoxy-aluminumhydride. After stirring for 1 h at room temperature the mixture was treated with water and neutralized by addition of 2N HCl. The product was extracted with ethyl acetate and chromatographed over silicagel (heptane/ethylacetate 8/2 as eluent). This provided 0.56 g of 3β alcohol 21 (Mp 121-123° C.) and 0.24 g of 3α alcohol 22 (Mp 84-87° C.). R$_f$ 0.53 (21) and 0.45 (22), heptane/ethylacetate 1/1. NMR (3αOH) 3.82 (m, CHOH); (3β OH) 4.08 (m, CHOH).

Compound 23

To a solution of lithium hexamethyldisilazide (prepared from 1.9 ml of 1.6M BuLi-hexane solution and 0.71 ml of hexamethyldisilazane in 4 ml of dry THF) was added at −40° C. 1 g of 18 and 0.7 ml of DMPU in 5 ml of THF. The mixture was stirred for 0.5 hr at −40° C. and then 225 ul of CH$_3$I was added by syringe. After stirring for an additional 0.5 h at −40° C. the reaction was completed. The mixture was diluted with water and extracted with ethylacetate. Chromatography of the crude product thus isolated gave 1.3 gr of 23, R$_f$ 0.43 (heptane/ethylacetate 8/2). NMR 1.10 (d, 3, 16αCH$_3$), 1.06 (s, 3, CH$_3$), 3.23 (2×s, 6, OCH$_3$), 5.0 (m, 2, allyl CH2), 5.78 (m, 1, allyl CH).

Compound 24

According to the procedure described for the preparation of 19, 1.3 g of 23 were converted into the required 24, to provide 1.2 g, R$_f$ 0.46 (heptane/ethylacetate 7/3) R$_f$ (s, 1, acetylene), 1.06 (s, 3, CH$_3$), 1.17 (d, 3, 16αCH$_3$).

Compound 25

To a solution of 800 mg of 24 in 20 ml of ethanol was added a solution of 80 mg of oxalic acid in 5 ml of water. The mixture was stirred for 1 h and then neutralized by addition of NaHCO$_3$. After dilution with water and extraction with ethylacetate 0.7 g of 25 remained as crystalline material. R$_f$ 0.47 (heptane/ethylacetate 7/3). NMR 2.78 (AB, 2, H4), 1.08 (s, 3, CH$_3$), 1.18 (d, 3, 16αCH$_3$), 2.67 (s, 1, acetylene).

Compounds 26, 27

To a solution of 725 mg of 25 in 20 ml of a 1/1 mixture of ethanol and THF was added 130 mg of sodiumborohydride. After stirring for 1 h 2 ml of acetone were added to destroy some excess reagent. After 15 min the mixture was poured into water and the product was extracted with ethylacetate. The material thus obtained was purified by chromatography at silicagel, using either methylenechloride-acetone or hexane-ethylacetate as eluent. This gave 300 mg of 27 (3α-OH) and 75 mg of 26 (3β—OH). R$_f$(26) 0.47 (methylenechloride/acetone 95/5). R$_f$ (27) 0.54 (methylenechloride/acetone 95/5). NMR (27) 3.82 (m, 1, 3βH), 2.75 (s, 1, acetylene), 1.06 (s, 3, CH$_3$), 1.17 (d, 3, 16αCH$_3$); (26) 4.07 (m, 1, 3βH), 2.76 (s, 1, acetylene), 5.01 (m, 2, CH$_2$ allyl), 5.78 (m, 1, CH-allyl).

Example 3

Compounds are tested for their estrogen receptor activity in a binding assay and in a transactivation assay.

Determination of competitive binding to cytoplasmic human estrogen receptor α or β from recombinant CHO cells is used to estimate the relative affinity (potency ratio) of a test compound for estrogen receptors present in the cytosol of recombinant Chinese hamster ovary (CHO) cells, stably transfected with the human estrogen receptor α (hERα) or β receptor (hERβ), as compared with estradiol (E$_2$).

The estrogenic and antiestrogenic activity of compounds is determined in an in vitro bioassay with recombinant Chinese hamster ovary (CHO) cells stably co-transfected with the human estrogen receptor α (hERα) or β receptor (hERβ), the rat oxytocin promoter (RO) and the luciferase reporter gene (LUC). The estrogenic activity (potency ratio) of a test compound to stimulate the transactivation of the enzyme luciferase mediated via the estrogen receptors hERα or hERβ is compared with the standard estrogen estradiol. The antiestrogenic activity (potency ratio) of a test compound to inhibit the transactivation of the enzyme luciferase mediated via the estrogen receptors hERα or hERβ by the estrogen estradiol is compared with the standard ICI 164.384 (=(7α,17β)-N-butyl-3,17-dihydroxy-N-methylestra-1,3,5(10)-triene-7-undecanamide).

Results

A quantitative parameter for agonist selectivity is obtained by dividing the percentage agonist activity for ER α by the percentage agonist activity for ER β. Compound 11a has agonist selectivity for estrogen receptor α over estrogen receptor β of more than 86 times. Compound 26 has an agonist selectivity for ER α over ER β of 59 times. Compound 27 has agonist selectivity of 88.3 times.

What is claimed is:

1. A 16α-substituted steroidal compound having formula 1,

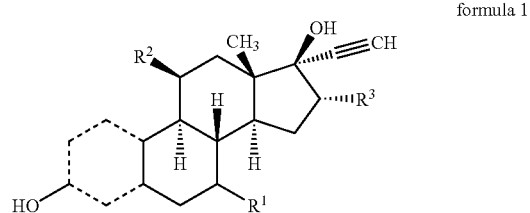

formula 1 wherein:
the dotted ring is a fully aromatic or a saturated ring with a Δ5-10 double bond;
R$^1$ is (C$_1$-C$_3$)alkyl or (C$_2$-C$_3$)alkenyl, and each of these groups can be substituted with one or more halogens;
R$^2$ is (C$_1$-C$_4$)alkyl, (C$_2$-C$_4$)alkenyl or methylene, and each of these groups can be substituted with one or more halogens;
R$^3$ is methyl or ethyl.

2. The 16α-substituted steroidal compound according to claim 1, wherein the halogens in R$^1$ and R$^2$ are selected from a group consisting of chlorine and fluorine.

3. The 16α-substituted steroidal compound according to claim 1, wherein R$^2$ is (C$_1$-C$_2$)alkyl or vinyl.

4. A pharmaceutical composition comprising: the compound according claim 1 and a pharmaceutically acceptable auxiliary.

* * * * *